(12) United States Patent
Van Bockel

(10) Patent No.: US 6,743,180 B1
(45) Date of Patent: *Jun. 1, 2004

(54) PRESSURE SENSOR FOR USE IN AN ARTERY

(75) Inventor: J. Hajo Van Bockel, Leiden (NL)

(73) Assignee: Rijksuniversiteit Leiden, Leiden (NL)

( * ) Notice: Subject to any disclaimer, the term of this patent is extended or adjusted under 35 U.S.C. 154(b) by 56 days.

This patent is subject to a terminal disclaimer.

(21) Appl. No.: 09/642,132

(22) Filed: Aug. 18, 2000

Related U.S. Application Data

(63) Continuation of application No. 09/134,746, filed on Aug. 14, 1998, now Pat. No. 6,159,156.

(30) Foreign Application Priority Data

Aug. 15, 1997 (EP) .............................. 97202523

(51) Int. Cl.$^7$ ........................... A61M 29/00; A61B 5/02
(52) U.S. Cl. ........................ 600/505; 600/462; 600/468; 606/191; 606/194
(58) Field of Search ................................. 623/1.1–1.12, 623/1.36, 1, 12, 11; 600/300–301, 484–486, 505, 462, 465, 468, 479, 480; 128/897–898; 606/191, 194, 198

(56) References Cited

U.S. PATENT DOCUMENTS 5,833,603 A * 11/1998 Kovacs et al. .............. 600/317
6,053,873 A * 4/2000 Govari et al. ............... 600/505
6,299,636 B1 * 10/2001 Schmitt et al. .............. 623/1.2

* cited by examiner

Primary Examiner—Max F. Hindenburg
Assistant Examiner—Michael Astorino
(74) Attorney, Agent, or Firm—TraskBritt

(57) ABSTRACT

A device for introduction into an animal or human body, especially into an artery. The device is preferably positioned in an aneurysmal sac in an artery between the wall of the artery and the wall of an endoprosthesis. The device has at least a pressure sensor and transducer for wirelessly transmitting data available from the pressure sensor.

44 Claims, 3 Drawing Sheets

PRESSURE SENSOR FOR USE IN AN ARTERY

CROSS REFERENCE TO RELATED APPLICATIONS

This application is a continuation of U.S. patent application Ser. No. 09/134,746 filed on Aug. 14, 1998, now U.S. Pat. No. 6,159,156, issued Dec. 12, 2000, which claims the benefit of European patent application EP 97202523.3, filed Aug. 15, 1997.

BACKGROUND OF THE INVENTION

The invention relates to a device for introduction into a human or animal body, especially into an artery for use as a pressure-sensing device.

In the arteries of human and animal bodies, one of the major problems is the loss of strength of the wall of the arteries, which can result in aneurysm formation. An aneurysm may endanger the health of human or animals because of the risk of internal bleeding which often results in death of the patient. Therefore, aneurysms are usually treated before rupture occurs by vascular prostheses, which replace the aneurysmal artery, thus excluding the aneurysm from the circulation.

A new development is the treatment by a so-called endoprosthesis.

Such endoprostheses are well known to the person skilled in the art and can, for example, be positioned within an artery by means of a number of stents. Although the procedure can be safely performed now, endoleakage is still a major problem immediately following the operation even up to many months following surgery. Endoleakage is the incomplete sealing of the arterial wall by the endoprosthesis. Endoleakage can result in a pressure build-up within the aneurysmal sac, enclosed between the wall of the artery and the endoprostheses. Monitoring endoleakage is universally performed by visualization of the endoleakage by means of, for example, a CT-scan, magnetic resonance, duplex ultrasound, and the like. Unfortunately, failure to visualize an endoleak does not exclude the presence of such an endoleak. Also, without a visible endoleak, the aneurysmal sac can still be under pressure with the danger of ultimate rupture and said internal bleeding. Failure to visualize endoleakage can, for example, result from failure to introduce sufficient contrast fluid into the aneurysmal sac that has been filled with a thrombus. This will mean that either no, or a relatively small amount of, blood will leak into the aneurysmal sac, resulting in pressure (without flow) to the arterial wall that may result in rupture. Of course, measuring pressure would be an ideal test to evaluate the absence of an endoleak. However, because of the invasive character of pressure measurement, direct pressure measurements can only be obtained during surgery.

BRIEF SUMMARY OF THE INVENTION

The present invention includes a device for measurement of the pressure within a human or animal body, more specifically in an artery, especially in an aneurysmal sac in an artery between the wall of the artery and the wall of an endoprosthesis. To that effect, a device according to the present invention is characterized by the features of the ensuing claims.

In this application, arteries have to be understood broadly, including, at least, arteries, veins and other blood vessels.

A device according to the present invention can be introduced into a human or animal artery, especially into an aneurysmal sac. The pressure sensor can provide pressure-related data that can be transmitted to a receiving means outside the human or animal body by means of the transponder. Wireless transmission of the data has the advantage of eliminating the need for wires extending from the pressure sensor to the skin of an animal or human. Whenever it is indicated, the pressure data can be obtained from the pressure sensor. These data can be used for the evaluation of pressure that may still be (or has developed again) within the aneurysmal sac. Thus, it is useful for assessment of the state of the artery and the risks of possible rupture of the aneurysm. The device is preferably energized by means of an electrical and/or magnetic field, energizing the device through the transponder. This means that it will not be necessary to provide the device with a battery, enhancing the safety of the human or animal and prolonging the time of use of the device.

In a preferred embodiment a device according to the present invention is characterized by the features of claim 2.

Introduction of the device into an artery through a catheter has the advantage that only a very small operation is necessary for introduction of the device. A catheter can for example be introduced into the artery by using a hollow needle which can be introduced into an artery in for example a leg. Subsequently, through this catheter the device can be introduced and directed to the proper position. The device can be pushed through the same catheter into position as the endoprosthesis, which is used for treatment of the aneurysms if necessary. This will render major operation or additional unnecessary.

Means for storing data, at least connected to at least the transponder, provides for the possibility for storing data taken from the pressure sensor over a prolonged period. Recording such data makes it very easy to obtain information about the occurrence of pressure differences and changes within the artery during that period of time without the necessity of numerous and repetitious measurements by means of a magnetic or electric field and transmitting and receiving means.

Means for positioning the device in a stable position within the artery, especially within an aneurysmal sac, makes easy, stable and secure positioning of the device possible. Such positioning has the advantage that the device will not change its position, at least not significantly, thus enabling even better recording of the pressure data. Comparison of the data will, therefore, be improved.

The invention further relates to device according to the present invention, an endoprosthesis, and, more specifically, an endovascular prosthesis for use in the abdomen.

Prevention of rupture of aneurysmal sacs is especially vital within the abdomen of human and animal bodies. Internal bleeding, especially within the abdomen, can very easily and quickly lead to the death of a human or animal. Thus, adequate recording of the pressure in such aneurysms can be lifesaving.

Means for exciting the transponder when positioned in an artery and for reading the data transmitted from the device to the outside of a human or animal body enable easy and noninvasive measurement of the pressure within the body, especially in an aneurysmal sac in an artery. Such measurements will provide proper and accurate data about the state of the artery, which can be vital to the life of the human or animal.

The present invention further relates to the use of a miniaturized pressure sensor and transponder attached thereto, for introduction into a human or animal artery.

The invention further relates to a method for measuring pressure in an artery of a human or animal body, especially in an aneurysmal sac therein.

Use of a method according to the present invention enables easy and accurate measurement of the pressure within an artery without the necessity of massive operation or repetitive scanning of the relevant parts of the body comprising contrast fluids or the like. A method according to the present invention is thus both patient-friendly and cost-effective for the animal or human.

The pressure sensor and transponder, as well as the endoprothesis, can be brought into position by using a catheter introduced through a hollow needle or the like. Such an operation is nontraumatic and can be performed quickly, easily and accurately.

Furthermore, the present invention relates to the use of a catheter for introduction of a sensor and a transponder into a human or animal body.

BRIEF DESCRIPTION OF THE DRAWINGS

To further clarify the invention exemplary embodiments of a device and a set method according to the present invention will be described hereafter, with reference to the drawings.

DETAILED DESCRIPTION OF THE INVENTION

In the following detailed description corresponding parts have corresponding reference signs. Measurements and values, as well as the illustrated embodiments, are merely presented as examples and are not to be interpreted as limiting the scope of the present invention.

Figure 1:
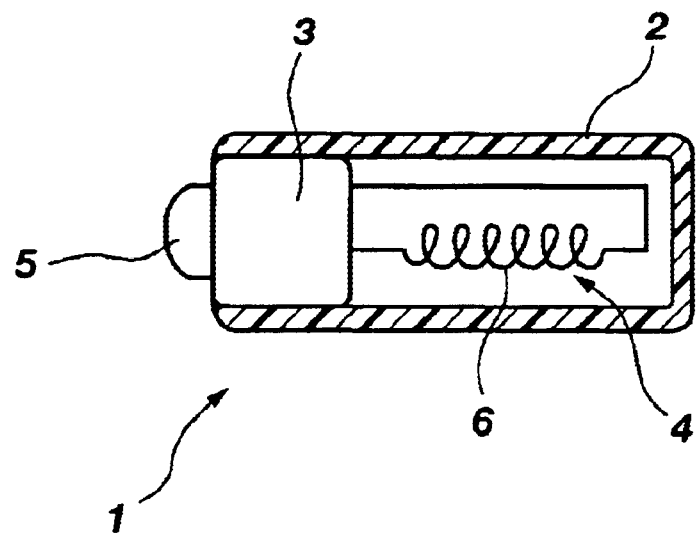
FIG. 1 is a cross-sectional schematic depicting a first embodiment of a pressure-sensing device according to the present invention for introduction into a human or animal artery.

FIG. 1 shows, at an enlarged scale and in cross-section, a device for introduction into a human or animal artery for use as a pressure sensing device. The device 1 comprises a housing 2, preferably made of biocompatible plastic, both air and liquid tight. The housing 2 encloses a pressure sensor 3 connected to a transponder 4. The pressure sensor means 3 comprises a pressure-sensing element 5, extending at least partly outside the housing 2. The pressure-sensing element 5 can be of any suitable type, for example, piezo-electric, membrane, strain gauge or capacity operated or the like. The measurement range has to be sufficient to measure normal and high pressures in an artery. For example, a measurement range for use in a main artery could be from 0 to 220 mm Hg ($29.3 \ast 10^3$ Pa), more specifically 50–150 mm Hg ($6.67 \ast 10^3 - 20 \ast 10^3$ Pa). A suitable range and sensitivity of the pressure-sensing element 5 can be readily chosen by the person skilled in the art.

The transponder comprises, in the embodiment as shown in FIG. 1, a coil 6 to be energized by an external electromagnetic field, inducing the transponder 4 to transmit a signal carrying data obtained from the pressure sensor 3. The signal transmitted by the transponder 4, can be received outside the human or animal body, the pressure data thus readily available for interpretation by means of, for example a suitable computer or the like. Under certain circumstances, it can be sufficient to assess whether the pressure within the artery is higher or lower than a boundary pressure, in which case the data can be transformed to an on/off signal for, for example, a LED. The form of the transponder depends inter alia on the intended use of the device, especially the intended position during use and the relevant animal or human body. Appropriate choices will be readily understood by the person skilled in the art.

Figure 4:
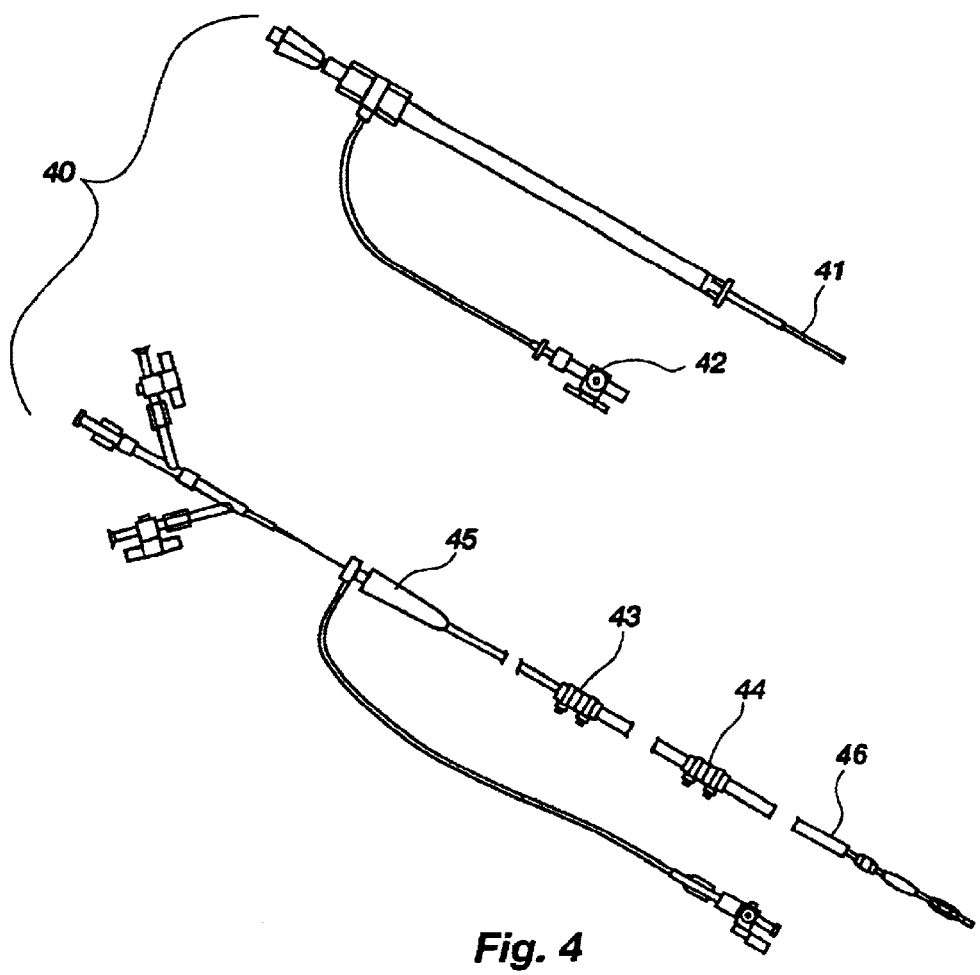
FIG. 4 depicts a catheter used for introduction of a pressure-sensing device and an endoprosthesis into an artery of a human or animal body.

By miniaturization, a device according to the present invention is made suitable for introduction into an artery, using a standard or specialized catheter 40 as shown, for example, in FIG. 4, comprising a guide tube 41, a stop cock 42, appropriate pushers 43, 44, stop valves 45, outer sheath 45, and the like. In FIG. 1, the outer dimensions of the housing 2 are, for example, 1 to 3 mm in diameter and 2 to 4 mm in length. However, the outer dimensions can be chosen depending on the position within the animal or human body. These methods and means are well known to a person skilled in the art.

Figure 2:
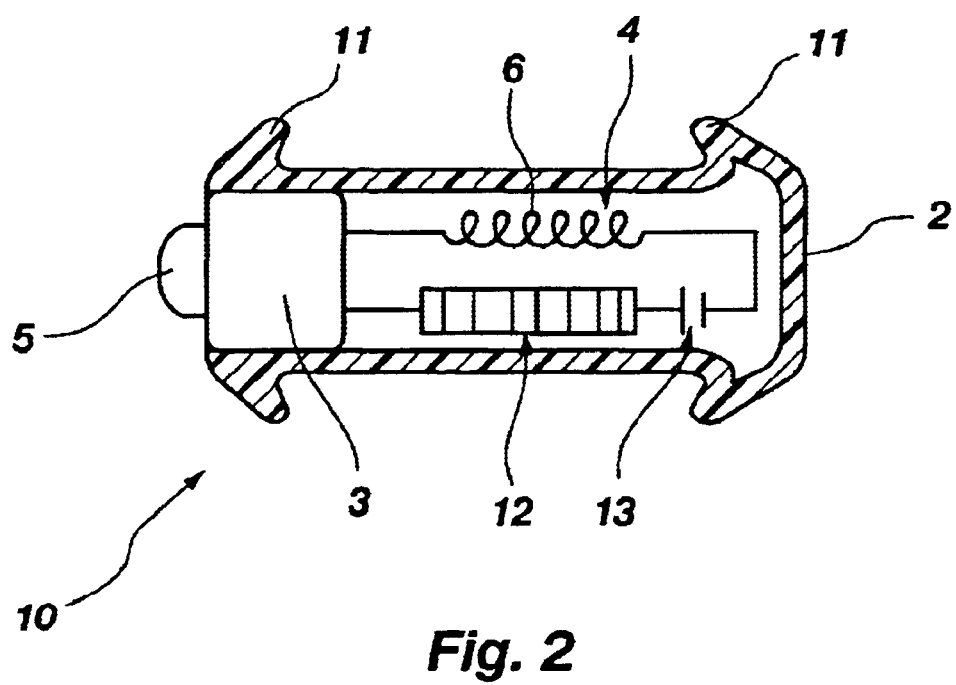
FIG. 2 is a cross-sectional schematic of a second embodiment of a pressure-sensing device according to the present invention.

FIG. 2 shows an alternative embodiment of a device according to the present invention.

In this embodiment, a device 10 comprises hook- or ring-shaped elements 11 extending from the outside of the housing 2, which elements 11 are suitable for obtaining a stable position of the device 10 within, for example, clogged blood in an aneurysmal sac or to an endoprosthesis, as will be explained later in connection with FIG. 3. In the embodiment as shown in FIG. 2, the pressure sensor 3 is again connected to a transponder 4, comprising, for example, a coil 6 for energizing the device and transmitting data to the outside of said animal or human body. Furthermore, the device 10 comprises means for storing data 12 and energy source 13, for example, a capacitor or a battery. The capacity of the energy source 13 has to be suitable to energize at least the pressure sensor 3 and the means for storing data 12 during a prolonged time span, for example, one or more days or weeks. With a device 10 according to FIG. 2, during a prolonged time span, pressure data can be obtained at intervals and stored in the means for storing data 12. After the prolonged time span, the transponder can be activated for transmitting the data stored in the means for storing data 12, providing data about the actual pressures measured within the artery as well as changes during said prolonged time. In a preferred embodiment, the energy source 13 can be energized by means of the transponder 4 using an electromagnetic field. If the data only has to be obtained during a relatively short time after introduction of the device 10 into an artery, a small battery can be sufficient.

Figure 3:
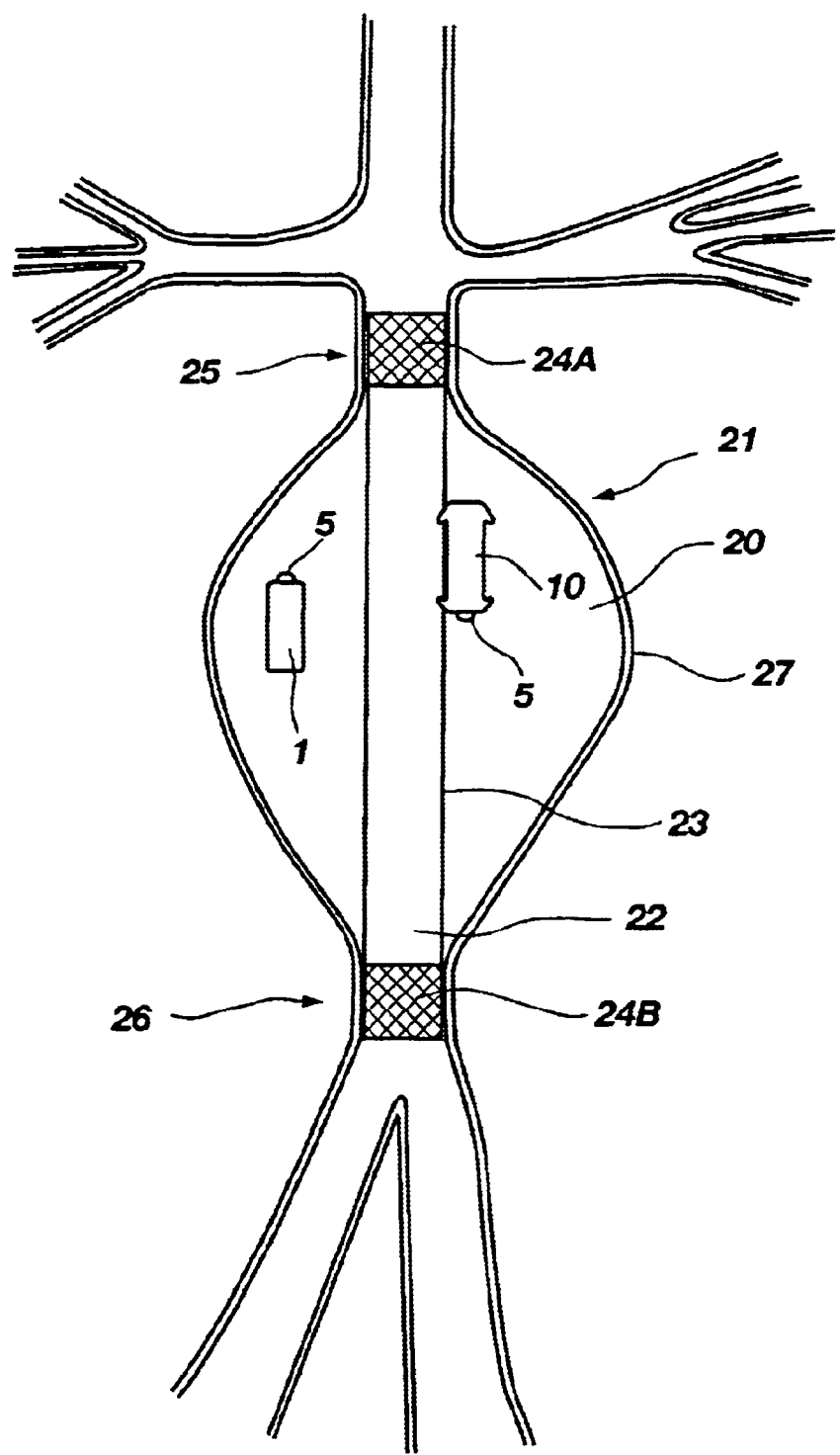
FIG. 3 schematically depicts pressure-sensing devices according to the present invention, positioned in an aneurysmal sac and excluded from the circulation by an endoprosthesis.

Device 1, 10 according to the present invention is especially suitable for measurement of pressure within an aneurysmal sac 20 in an artery 21, for example, an artery in the abdomen of a human body as shown in FIG. 3.

An aneurysm is dangerous to the health of a human or animal since rupture of an artery would lead to internal bleeding with possibly lethal consequences. In order to negate this risk, endoprostheses are used for bridging aneurysms. In FIG. 3, a tube endoprosthesis is shown positioned within an artery 21. The endoprosthesis 22 comprises a flexible, closed wall 23 and is provided fully, or at both ends, with a stent 24A, 24B. A first end 25 of the endoprosthesis is positioned within the artery 21 at the upstream side of the aneurysm 20 by means of the stent 24A, the second end 26 at the opposite, downstream side of the aneurysm by means of the second stent 24B. An endoprosthesis of this type is known in the state of the art and is, for example, manufactured under the registered trademark VANGUARD by the Meadox Boston Scientific Corporation, USA. However, all kinds of endoprostheses can be used, for example, a tube, bifurcated, uni- or bilateral protheses. A device 1, 10 according to the present invention is introduced into the aneurysmal sac 20 between the wall 27 of the aneurysmal sac and the endoprosthesis 22. In FIG. 3, a device 1 according to FIG. 1 is positioned left of the endoprosthesis within clotted blood in the aneurysmal sac. In the same FIG. 3, a device 10 according to FIG. 2 is positioned within the aneurysmal sac 20 to the right of the endoprosthesis 22 and is attached to the endoprosthesis by means of the hook- or ring-shaped elemenent 11. These positions are only shown in one figure for elucidation purposes and might normally not be combined. Other means for positioning a device according to the present invention within an aneurysmal sac or a blood vessel can be used in any suitable manner.

A device according to the present invention can be introduced into an artery, especially into an aneurysmal sac 20, using catheter 40, for example, as shown in FIG. 4, through which the endoprosthesis 22 with the stents 24A, 24B also can be introduced. As shown in FIG. 4, catheter 40 includes cartridge guide tube 41, stop cock 42, hemostasis valve 45, iliac pusher 43, aorta pusher 44, and outer sheath 46 (with a nose cone). As appropriate, the device 1, 10 is first introduced into the clogged blood in the aneurysmal sac 20, after which the endoprosthesis is brought into position and fixated with the stents 24, 24B. It is, of course, also possible to position a device according to the present invention in an artery or other, body part during an operation in which at least one incision is made in the body.

Use of the device, 10 positioned in the aneurysmal sac 20 provides the ability to monitor any changes in the pressure within the aneurysmal sac 20, which could be an indication of leakage of blood into the aneurysmal sac 20, passing either one of the stents 24A, 24B or endoleak transmitting pressure into the aneurysmal sac 20 without blood transfer. If the pressure measured within the aneurysmal sac 20 becomes too high or changes significantly, correction of the position of the endoprosthesis 22 and/or the stents 24A, 24B may be necessary. Since the pressure detection noninvasive and very local during use, outpatient monitoring of a patient's blood pressure after positioning of the endoprosthesis 22 is easily possible. Especially when a device according to FIG. 2 is used, sufficient data can be obtained without undue burden to the human or animal.

Figure 5:
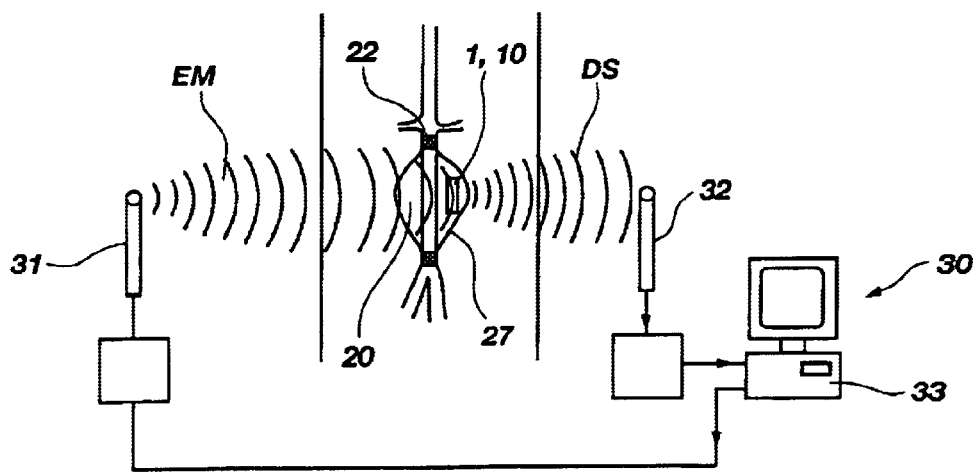
FIG. 5 schematically illustrates a method according to the invention for reading data measured by the pressure-sensing device.

FIG. 5 is a schematic illustration of a device 30 for activating the transponder 4 of the pressure-sensing device 1, 10 within an aneurysmal sac 20 and for receiving the data signals transmitted by the transponder 4. This device 30 comprises a first antenna 31 for providing an electromagnetic field (EM) for energizing the transponder 4. Furthermore, the device 30 comprises a second antenna 32 for receiving the data signals DS transmitted wireless by the transponder 4. The first antenna 31 and second antenna 32, which can be of any suitable form and dimension and can also be combined in one antenna, are connected to control means, for example a computer 33. The computer program helps to read the data from the data signals and transforming these into readable signals, for example a blood pressure graph on the computer screen or a print out.

In a further embodiment, not shown in the drawings, energy means are provided which can be energized by blood pulses within the artery, resulting from the normal heartbeats. This can, for example, be piezo-electrical means, pressure-sensitive membranes, or the like, which can generate sufficient energy to at least energize the means for storing data 12.

The present invention is by no means limited to the embodiments as described in the description and shown in the figures. Many alternatives are possible.

For example, other means for introduction of a device into an artery of a human or animal body can be used, whereas a pressure-sensing device according to the present invention can also be positioned in other arteries or different parts of the body, with or without an endoprosthesis. Furthermore, more than one pressure-sensing device according to the present invention can be introduced into one aneurysmal sac, for example, for obtaining data from various positions within the aneurysmal sac. Moreover, different means for positioning of a device according to the present invention within a human or animal body can be appropriately used. A housing of a device according to the present invention can be made of any suitable material and is preferably mainly massive, for example, made of biocompatible foam or the like. Each device can be multifunctional, for example, comprising further sensor means, such as temperature-sensing means, which can be connected with a further transponder having different transponding characteristics.

These and many similar variations are considered to fall within the scope of the present invention.

What is claimed is:

1. A device for introduction into an aneurysmal sac of an artery of a human or animal body between the wall of the artery and the wall of an endoprosthesis disposed in the artery, said device comprising: at least a pressure sensor and a transponder for wirelessly transmitting data available from the pressure sensor, said pressure sensor and said transponder each being configured to be positioned inside the aneurysmal sac.

2. The device of claim 1, wherein the device has outer dimensions such that it can be introduced into the artery through a catheter.

3. The device of claim 1, wherein the pressure sensor and the transponder are interconnected.

4. The device of claim 1, wherein the pressure sensor has a range of at least 50–150 mm Hg ($6.67*10^3$ Pa–$20.0*10^3$Pa).

5. The device of claim 1, further comprising means for storing data available from the pressure sensor, said means connected at least to the transponder.

6. The device of claim 1, further comprising a stabilizer for positioning the device in a stable position within the aneurysmal sac.

7. The device of claim 6, wherein the stabilizer is configured to position the device at least partly within blood clogged in the aneurysmal sac.

8. The device of claim 6, wherein the stabilizer is configured to position the device at least partly on the endoprosthesis.

9. The device of claim 1, wherein the pressure sensor and the transducer are contained within the same housing.

10. The device of claim 1, wherein the pressure sensor has a range of at least 25–175 mm Hg ($3.3*10^3$ Pa–$23.3*10$ Pa).

11. The device of claim 1, wherein the pressure sensor has a range of at least 0–220 mm Hg (0–$29.3*10^3$ Pa).

12. A kit comprising:
   a device for introduction into an aneurysmal sac of an artery of a human or animal body between the wall of the artery and the wall of an endoprosthesis disposed in the artery, said device comprising:

a pressure sensor, and a transponder for wirelessly transmitting data available from the pressure sensor, said pressure sensor and said transponder each being configured to be positioned inside the aneurysmal sac; and an endoprosthesis.

13. The kit of claim 12, wherein said endoprosthesis is an endovascular prosthesis for use in the abdomen.

14. The kit of claim 12, further comprising:

means for exciting the transponder when positioned in an artery of a human or animal; and means for reading data transmitted from the pressure sensor and/or data means through the transponder to the outside of the human or animal.

15. The kit of claim 12, further comprising means for introduction into an artery, through which the device is introduced into the artery.

16. The kit of claim 15, wherein the means for introduction comprises means for positioning the device in an aneurysmal sac.

17. The kit of claim 15, wherein the means for introduction comprises a catheter.

18. The kit of claim 17, wherein the device is configured to fit into a lumen of the catheter.

19. A kit of parts comprising the following components:

(i) a device for introduction into an aneurysmal sac of a mammalian artery between the wall of the mammalian artery and the wall of an endoprosthesis disposed in the mammalian artery, said device comprising:

a pressure sensor, and a transponder for wirelessly transmitting data provided by the pressure sensor, said pressure sensor and said transponder each being configured to be positioned within the aneurysmal sac;

(ii) an endovascular prosthesis;

(iii) means for exciting the transponder when positioned in the mammalian artery;

(iv) means for externally interpreting data transmitted from the transponder; and (v) a catheter through which the device is to be introduced into the mammalian artery, said catheter including means for positioning the device in an aneurysmal sac, said device further having been configured to fit into the catheter's lumen.

20. The device of claim 2, wherein the device has an outer diameter of approximately 1 mm to approximately 3 mm and an outer length of approximately 2 mm to approximately 4 mm.

21. The device of claim 6, wherein the stabilizer comprises a ring shaped element.

22. A device for introduction into an aneurysmal sac of an artery of a human or animal body between the wall of the artery and the wall of an endoprosthesis disposed in the artery, said device comprising:

a pressure sensor;

a transponder for wirelessly transmitting data available from the pressure sensor; and means for storing data available from the pressure sensor, the means for storing data connected at least to the transponder;

the pressure sensor, the transponder, and the means for storing data each being configured to be positioned inside the aneurysmal sac.

23. The device of claim 1, further comprising a housing in which both the pressure sensor and the transponder are disposed, the housing being made of biocompatible plastic.

24. A device for monitoring pressure in an aneurysmal sac of an artery of a human or animal, the aneurysmal sac comprising a space between a wall of the artery and a wall of an endoprosthesis disposed in the artery, the device comprising:

a housing configured to be positioned inside the aneurysmal sac;

a pressure sensor disposed in the housing, the pressure sensor comprising a pressure sensing element extending at least partly outside the housing; and a transponder disposed in the housing.

25. The device of claim 23, wherein the device is configured to be introduced into the artery through a catheter.

26. The device of claim 25, wherein the device has an outer diameter of approximately 1 mm to approximately 3 mm and an outer length of approximately 2 mm to approximately 4 mm.

27. The device of claim 24, wherein the pressure sensor and the transponder are interconnected.

28. The device of claim 24, wherein the pressure sensor has a range of at least 50–150 mm Hg ($6.67 \times 10^3$ Pa–$20.0 \times 10^3$ Pa).

29. The device of claim 24, wherein the pressure sensor has a range of at least 25–175 mm Hg ($3.3 \times 10^3$ Pa–$23.3 \times 10^3$ Pa).

30. The device of claim 24, wherein the pressure sensor has a range of at least 0–220 mm Hg (0.0 Pa–$23.3 \times 10^3$ Pa).

31. The device of claim 24, further comprising means for storing data available from the pressure sensor, said means connected at least to the transponder.

32. The device of claim 24, further comprising a stabilizer for maintaining the device in a substantially stable position within the aneurysmal sac.

33. The device of claim 32, wherein the stabilizer comprises a ring shaped element.

34. The device of claim 32, wherein the stabilizer is configured to maintain the device in a substantially stable position at least partly within blood clogged in the aneurysmal sac.

35. The device of claim 32, wherein the stabilizer is configured to maintain the device in a substantially stable position at least partly on the endoprosthesis.

36. A kit comprising:

a device for monitoring pressure in an aneurysmal sac of an artery of a human or animal, the aneurysmal sac comprising a space between a wall of the artery and a wall of an endoprosthesis disposed in the artery, the device comprising:

a housing configured to be positioned inside the aneurysmal sac, a pressure sensor disposed in the housing, the pressure sensor comprising a pressure sensing element extending at least partly outside the housing, and a transponder disposed in the housing; and an endoprosthesis.

37. The kit of claim 36, wherein the endoprosthesis comprises an endovascular prosthesis for use in the abdomen.

38. The kit of claim 36, further comprising:

means for exciting the transponder when positioned inside the human or animal; and means for reading data transmitted from the pressure sensor through the transponder to the outside of the human or animal.

39. The kit of claim 36, further comprising means for introduction of the device into the artery.

40. The kit of claim 39, wherein the means for introduction comprises means for positioning the device in an aneurysmal sac.

41. The kit of claim 39, wherein the means for introduction comprises a catheter.

42. The kit of claim 41, wherein the device is configured to fit into the lumen of the catheter.

43. The kit of claim 42, wherein the device has an outer diameter of approximately 1 mm to approximately 3 mm and an outer length of approximately 2 mm to approximately 4 mm.

44. A kit comprising:
 a device for monitoring pressure in an aneurysmal sac of an artery of a human or animal, the aneurysmal sac comprising a space between a wall of the artery and a wall of an endoprosthesis disposed in the artery, the device comprising:
  a housing configured to be positioned inside the aneurysmal sac,
  a pressure sensor disposed in the housing; the pressure sensor comprising a pressure sensing element extending at least partly outside the housing, and
  a transponder connected to the pressure sensor disposed in the housing;
 a vascular endoprosthesis;
 means for exciting the transponder when positioned inside the human or animal;
 means for externally interpreting data transmitted from the pressure sensor through the transponder; and
 a catheter for introducing the device into the artery, the catheter including means for positioning the device in the aneurysmal sac, the device further being configured to fit into the lumen of the catheter.

* * * * *

UNITED STATES PATENT AND TRADEMARK OFFICE
CERTIFICATE OF CORRECTION

PATENT NO. : 6,743,180 B1  
APPLICATION NO. : 09/642132  
DATED : June 1, 2004  
INVENTOR(S) : Van Bockel It is certified that error appears in the above-identified patent and that said Letters Patent is hereby corrected as shown below:

| | |
|---|---|
| COLUMN 2, LINES 18-19, | delete "In a perferred embodiment a device according to the present invention is characterized by the features of claim 2." |
| COLUMN 2, LINE 23, | change "using" to --inserting-- |
| COLUMN 2, LINE 24, | change "which can be introduced into" to --through-- |
| COLUMN 2, LINE 27, | after "be pushed" insert --into position-- and after "catheter" delete "into position" |
| COLUMN 2, LINE 28, | change "endoprosthesis, which" to --endoprosthesis that-- |
| COLUMN 2, LINE 29, | after "major" delete "operation" |
| COLUMN 2, LINE 30, | after "additional" insert --surgery-- |
| COLUMN 2, LINE 31, | after "connected to" delete "at least" |
| COLUMN 2, LINE 47, | after "relates to" insert --a-- |
| COLUMN 3, LINE 23, | after "device and" and delete "a set" |
| COLUMN 3, LINE 56, | after "pressure sensor" delete "means" |
| COLUMN 4, LINE 1, | after "transponder" insert --4-- |
| COLUMN 5, LINE 34, | change "stents 24," to --stents 24A,-- |
| COLUMN 5, LINE 38, | change "device," to --device 1,-- |
| COLUMN 5, LINE 60, | change "signals DS" to --signals (DS)-- and after "transmitted" delete "wireless" |
| COLUMN 5, LINE 63, | after "connected to" insert --a-- |
| COLUMN 5, LINE 64 | change "means," to --element,-- |
| COLUMN 5, LINE 65, | change "transforming" to --transforms-- |

Signed and Sealed this

Twenty-ninth Day of August, 2006

JON W. DUDAS  
*Director of the United States Patent and Trademark Office*